(12) United States Patent
Kim (10) Patent No.: US 10,516,868 B2
(45) Date of Patent: *Dec. 24, 2019

(54) HOLOPORTAL AND HOLOCLOUD SYSTEM AND METHOD OF OPERATION

(71) Applicant: DOUBLEME, INC., San Jose, CA (US)

(72) Inventor: Heekwan Kim, San Jose, CA (US)

(73) Assignee: DOUBLEME, INC., San Jose, CA (US)

( * ) Notice: Subject to any disclaimer, the term of this patent is extended or adjusted under 35 U.S.C. 154(b) by 222 days.

This patent is subject to a terminal disclaimer.

(21) Appl. No.: 15/206,255

(22) Filed: Jul. 9, 2016

(65) Prior Publication Data

US 2017/0013246 A1 Jan. 12, 2017

Related U.S. Application Data

(60) Provisional application No. 62/190,566, filed on Jul. 9, 2015.

(51) Int. Cl.
*G06T 1/20* (2006.01)
*G06T 15/00* (2011.01)
(Continued)

(52) U.S. Cl.
CPC ......... *H04N 13/111* (2018.05); *G03H 1/0443* (2013.01); *G03H 1/0476* (2013.01);
(Continued)

(58) Field of Classification Search
CPC .......... H04N 13/0011; H04N 13/0242; H04N 13/0275; H04N 13/0059; G06T 1/20;
(Continued)

(56) References Cited

U.S. PATENT DOCUMENTS

| 7,289,662 B2 * | 10/2007 | Keaton | G06K 9/00201 345/419 |
| 2002/0024517 A1 * | 2/2002 | Yamaguchi | A63F 13/10 345/424 |

(Continued)

*Primary Examiner* — Joseph G Ustaris
*Assistant Examiner* — Boubacar Abdou Tchoussou
(74) *Attorney, Agent, or Firm* — Invent Capture, LLC.; Samuel S. Cho (57) ABSTRACT

A novel electronic system provides fast three-dimensional model generation, social content sharing of dynamic three-dimensional models, and monetization of the dynamic three-dimensional models created by casual consumers. In one embodiment, a casual consumer utilizes a dedicated real-time 3D model reconstruction studio with multiple camera angles, and then rapidly create dynamic 3D models with novel computational methods performed in scalable graphics processing units. In another embodiment, uncalibrated multiple sources of video recording of a targeted object are provided by a plurality of commonly-available consumer video recording devices (e.g. a smart phone, a camcorder, a digital camera, etc.) located at different angles, after which the uncalibrated multiple sources of video recording are transmitted to a novel cloud computing system for real-time temporal, spatial, and photometrical calibration and 3D model reconstruction. The dynamic 3D models can be uploaded, listed, and shared among content creators and viewers in an electronic sharing platform.

3 Claims, 7 Drawing Sheets

200

RAPID THREE-DIMENSIONAL MODEL GENERATION FROM UNCALIBRATED MULTIPLE SOURCE OF VIDEO RECORDING OF A TARGET OBJECT AND SUBSEQUENT CLOUD COMPUTING-BASED VIDEO DATA CALIBRTION AND THREE-DIMENSIONAL RECONSTRUCTION OF THE TARGETED OBJECT (e.g. HOLOCLOUND)

(51) Int. Cl.

| | |
|---|---|
| *G06T 19/00* | (2011.01) |
| *H04N 13/111* | (2018.01) |
| *H04N 13/194* | (2018.01) |
| *H04N 13/243* | (2018.01) |
| *H04N 13/275* | (2018.01) |
| *H04N 21/2343* | (2011.01) |
| *H04N 13/246* | (2018.01) |
| *H04N 21/23* | (2011.01) |
| *H04N 13/10* | (2018.01) |
| *G16B 25/00* | (2019.01) |
| *G06T 17/20* | (2006.01) |
| *G06F 3/0481* | (2013.01) |
| *G03H 1/04* | (2006.01) |

(52) U.S. Cl.
CPC ............ *G06F 3/04815* (2013.01); *G06T 1/20* (2013.01); *G06T 15/005* (2013.01); *G06T 17/20* (2013.01); *G06T 19/006* (2013.01); *G16B 25/00* (2019.02); *H04N 13/10* (2018.05); *H04N 13/194* (2018.05); *H04N 13/243* (2018.05); *H04N 13/246* (2018.05); *H04N 13/275* (2018.05); *H04N 21/23* (2013.01); *H04N 21/2343* (2013.01); *G03H 2001/0452* (2013.01); *G06T 2200/04* (2013.01); *G06T 2200/24* (2013.01)

(58) Field of Classification Search
CPC ... G06T 17/20; G06T 19/006; G06T 2200/04; G06T 2200/24; G06F 3/04815; G03H 1/0476; G03H 1/0443; G03H 2001/0452
See application file for complete search history.

(56) References Cited

U.S. PATENT DOCUMENTS

| | | | | |
|---|---|---|---|---|
| 2002/0158873 | A1* | 10/2002 | Williamson | G06T 15/20 345/427 |
| 2004/0258309 | A1* | 12/2004 | Keaton | G06K 9/00201 382/190 |
| 2005/0088515 | A1* | 4/2005 | Geng | G06T 7/564 348/47 |
| 2011/0216160 | A1* | 9/2011 | Martin | H04N 5/89 348/40 |
| 2013/0038618 | A1* | 2/2013 | Urbach | G06F 9/5005 345/522 |
| 2014/0267571 | A1* | 9/2014 | Periyannan | H04N 7/15 348/14.08 |
| 2015/0022666 | A1* | 1/2015 | Kay | H04L 67/025 348/159 |
| 2016/0150217 | A1* | 5/2016 | Popov | G06T 15/04 348/48 |
| 2016/0284123 | A1* | 9/2016 | Hare | G06T 7/55 |

* cited by examiner

HOLOPORTAL AND HOLOCLOUD SYSTEM AND METHOD OF OPERATION

BACKGROUND OF THE INVENTION

The present invention generally relates to digital image processing. The present invention also relates to an improvement in functioning of one or more computers by improving digital image processing methods for computer-generated graphical objects. Furthermore, the present invention relates to three-dimensional (3D) image creation, sharing, and monetization. More specifically, the present invention relates to one or more electronic systems that provide rapid three-dimensional (3D) model generation, 3D model social content sharing, and monetization of 3D models in e-commerce and mobile ecosystems.

Wearable virtual reality (VR) devices, such as VR goggles and VR headsets, are increasingly being utilized in computer gaming, augmented reality, situation simulation training, and other applicable computerized applications in recent years. More than two hundred VR goggles are currently marketed as consumer electronics products with related electronic hardware to provide three-dimensional (3D) virtual reality graphical environment to users.

Unfortunately, conventional methods of virtual reality (VR) content creation is generally time-consuming and expensive, thus serving as a bottleneck to widespread adaptation and utilization by casual users who are not computer-graphics experts. For example, designing one animated 3D character for a computer game often costs approximately $500,000 USD with two months of graphical design refinements. Furthermore, the average cost of producing a 3D computer game to completion may cost up to $200 million USD with years of computer graphics work. In addition, 360-degree virtual reality video cameras, which are utilized to capture images of a real object (e.g. a human model or another desirable object for rendering) in various angles prior to rendering of the also-costly conventional 3D model generation, have equipment prices ranging from $1,500-$500,000 USD.

The high costs of 3D model production and related electronic equipment and an extensive time delay in 3D model generation are roadblocks to widespread and ubiquitous creation of 3D virtual reality contents in various electronic applications by casual users. Therefore, it may be beneficial to provide a novel electronic system that can inexpensively capture live objects and rapidly generate 3D models with common consumer video recording equipment and cloud computing resources. Furthermore, it may also be beneficial to provide multiple and flexible methods of capturing live objects to achieve fast real-time creation of 3D models. In addition, it may also be beneficial to provide a novel electronic platform that accommodates convenient sharing and monetization of casual user-created 3D models and related multimedia data.

SUMMARY

Summary and Abstract summarize some aspects of the present invention. Simplifications or omissions may have been made to avoid obscuring the purpose of the Summary or the Abstract. These simplifications or omissions are not intended to limit the scope of the present invention.

In a preferred embodiment of the invention, a three-dimensional body double-generating electronic system based on a cloud computing resource and consumer recording equipment is disclosed. This three-dimensional body double-generating system comprises: a plurality of consumer-level portable video recording devices positioned circularly around a target object at various angles relative to the target object, wherein the plurality of consumer-level portable video recording devices generates a plurality of multiple-angle video data streams; a scalable number of graphics processing units (GPU's) allocated to the cloud computing resource, wherein each graphics processing unit executes a pre-processing module and a 3D reconstruction module for calibrating, calculating, reconstructing, and generating graphical transformations to create a 3D body double model that resembles the target object from the plurality of multiple-angle video data streams; a wireless transceiver integrated into or connected to the plurality of consumer-level portable video recording devices, wherein the wireless transceiver is configured to transmit the plurality of multiple-angle video data streams from the plurality of consumer-level portable video recording devices to the scalable number of GPU's in the cloud computing resource; and the cloud computing resource comprising one or more cloud computing servers that include one or more GPU's, wherein the one or more cloud computing servers are connected to each other to formulate a scalable cloud computing network, and wherein the scalable cloud computing network allocates and manages the scalable number of GPU's to achieve a rapid creation of the 3D body double model based on a particular calculation load requirement for the graphical transformations associated with the target object.

Figure 1:
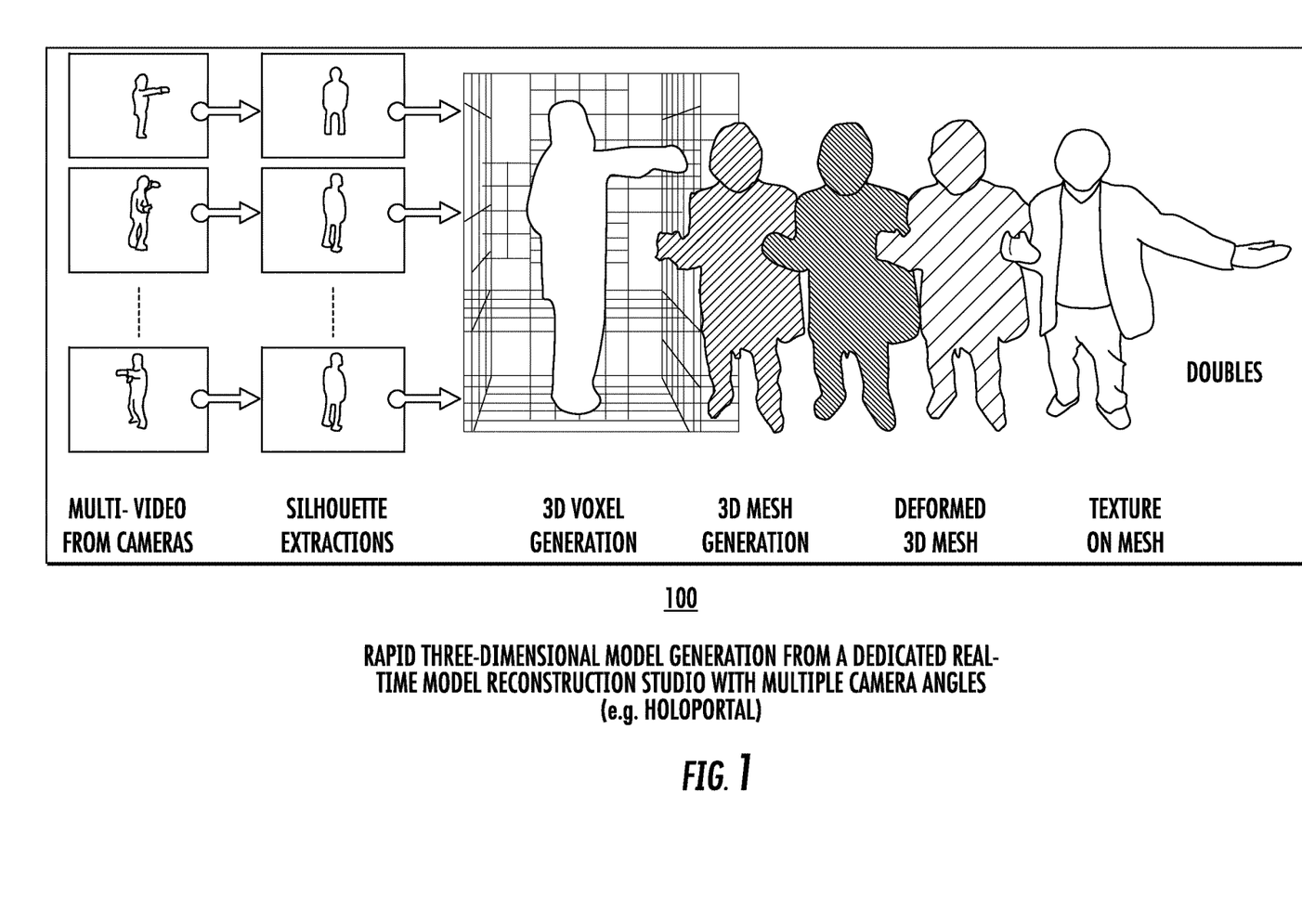
FIG. 1 shows a process diagram for rapid three-dimensional model generation from a dedicated real-time model reconstruction studio with multiple camera angles, in accordance with an embodiment of the invention.
Figure 3:
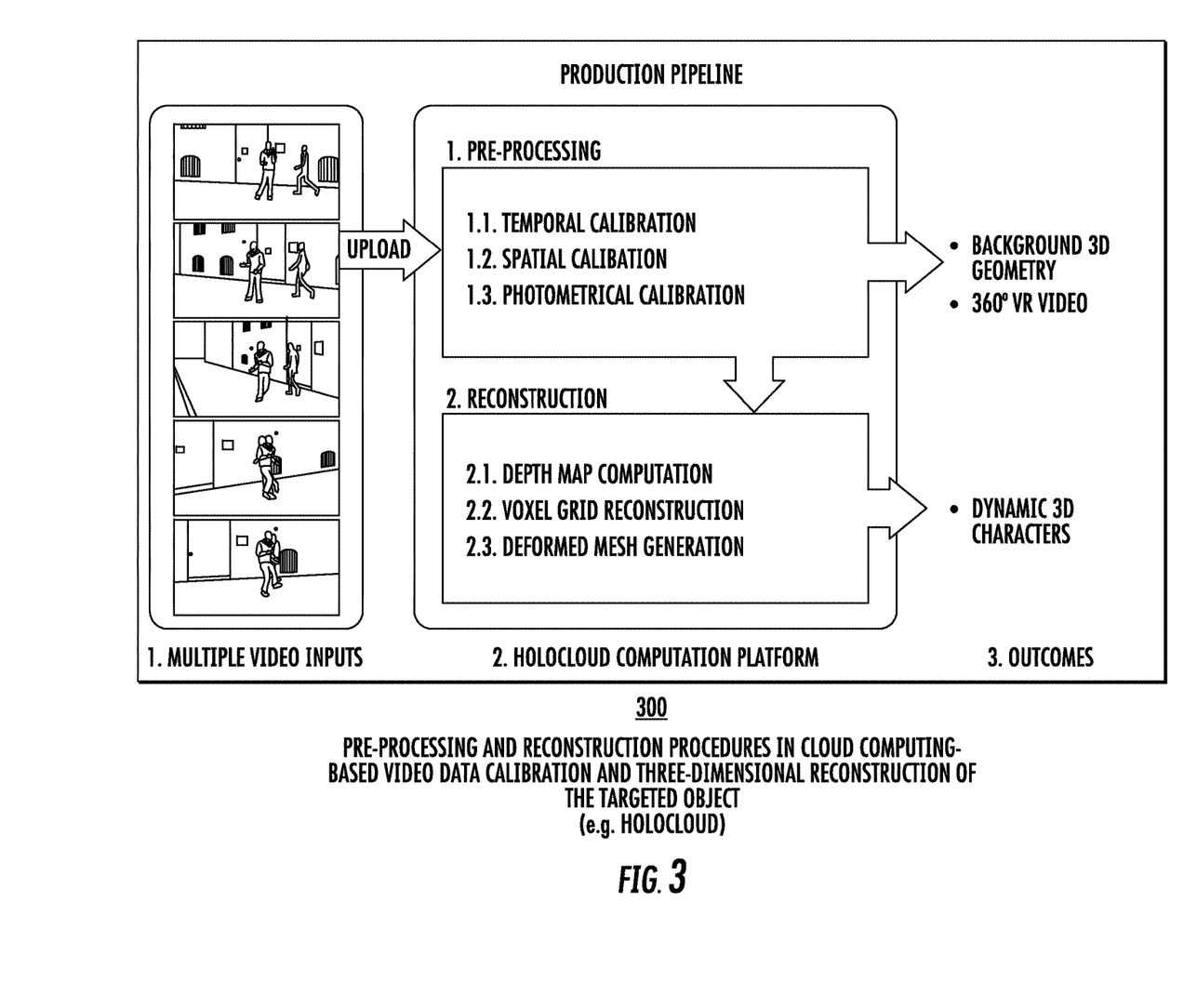
FIG. 3 shows pre-processing and reconstruction procedures in cloud computing-based video data calibration and three-dimensional reconstruction of the targeted object, in accordance with an embodiment of the invention.

Furthermore, in one embodiment of the invention, a dedicated real-time model reconstruction studio (e.g. "HoloPortal" studio) with multiple camera angles and graphics processing equipment captures a live video of a targeted object, and then rapidly create dynamic 3D models in real-time by applying a novel graphics processing algorithm (e.g. steps shown in FIG. 1 or FIG. 3).

In another embodiment of the invention, uncalibrated multiple sources of video recording of a targeted object are provided by a plurality of commonly-available consumer video recording devices (e.g. a smart phone, a camcorder, a digital camera, etc.) located at different angles, after which the uncalibrated multiple sources of video recording are transmitted to a novel cloud computing system (e.g. HoloCloud) for real-time temporal, spatial, and photometrical calibration and 3D model reconstruction.

Yet in another embodiment of the invention, a dynamic 3D model generated and reconstructed through the novel graphics processing algorithm in a HoloPortal system or a HoloCloud system is uploaded to a novel electronic platform that generates 3D virtual reality display and sharing user interfaces and database organization environment for dynamic 3D model content sharing and/or monetization.

Yet in another embodiment of the invention, a dynamic 3D model (e.g. a computerized 3D model in a virtual reality environment, a hologram, etc.) generated and reconstructed through the novel graphics processing algorithm in a HoloPortal system or a HoloCloud system is manufactured as a physical 3D model from a 3D printer or produced as a portable hologram that can be carried or reproduced from one location to another.

DETAILED DESCRIPTION

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

The detailed description is presented largely in terms of description of shapes, configurations, and/or other symbolic representations that directly or indirectly resemble one or more rapid three-dimensional model generation, social content sharing, monetization systems, and related methods of operation. In particular, various embodiments of the present invention directly or indirectly resemble one or more HoloPortal systems, HoloCloud systems, and methods of operating such systems. These process descriptions and representations are the means used by those experienced or skilled in the art to most effectively convey the substance of their work to others skilled in the art.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment. Furthermore, separate or alternative embodiments are not necessarily mutually exclusive of other embodiments. Moreover, the order of blocks in process flowcharts or diagrams representing one or more embodiments of the invention do not inherently indicate any particular order and do not imply any limitations in the invention.

One objective of an embodiment of the present invention is to provide a novel electronic system that can inexpensively capture multiple-angle videos of a target object, after which three-dimensional computerized models are rapidly generated in real time or near real time.

Furthermore, another objective of the present invention is to provide multiple and flexible methods of capturing target objects as video data and reconstructing 3D computerized models by utilizing either a dedicated professional-level 3D model portal studio or consumer video recording devices communicating with scalable cloud computing resources, wherein the consumer video recording devices are positioned in various angles relative to the target objects to capture multi-angle video footages prior to various calibration and computerized 3D model reconstruction by the scalable cloud computing resources.

In addition, another objective of the present invention is to provide a novel electronic information sharing and exchange platform that accommodates convenient 3D model contents sharing and monetization, especially for casual user-created 3D model contents.

Yet another objective of an embodiment of the present invention is to provide a business profit model for 3D content creators, electronic content sharing and monetization operators, and content viewers.

For the purpose of describing the invention, a term "three-dimensional model," or "3D model," is defined as one or more computer-generated three-dimensional images, videos, or holograms. In a preferred embodiment of the invention, a computerized 3D model is created after multi-angle video data are extracted, transformed, and reconstructed by three-dimensional graphics processing algorithms executed in a computer system or in a cloud computing resource comprising a plurality of networked and parallel-processing computer systems.

Furthermore, for the purpose of describing the invention, a term "cloud" is defined as a scalable data network-connected and/or parallel-processing environment for complex graphics computations, transformations, and processing. The data network-connected and/or parallel-processing environment can be provided using a physical connection, a wireless connection, or both. For example, a cloud computing resource comprising a first cloud computing server, a second cloud computing server, and/or any additional number of cloud computing servers can each extract and transform a portion of multi-angle video data simultaneously as part of a scalable parallel processing algorithm, which performs temporal, spatial, and photometrical calibrations, and executes depth map computation, voxel grid reconstruction, and deformed mesh generation. A scalable number of cloud computing servers enables a real-time or near real-time transformation and reconstruction of 3D models after consumer video recording devices transmit multi-angle video data to the cloud computing resource.

Moreover, for the purpose of describing the invention, a term "HoloPortal" is defined as a 3D model creation studio that incorporates cameras positioned on a multiple number of angles around a stage, where a target object is placed for video footage recording at the multiple number of angles around the stage. The 3D model creation studio also typically incorporates a real-time or near real-time 3D reconstruction electronic system, which is configured to perform silhouette extractions, 3D voxel generation, 3D mesh generation, and texture and detail-adding operations to create a user-controllable three-dimensional model that resembles the target object.

In addition, for the purpose of describing the invention, a term "HoloCloud" is defined as a novel electronic system that captures live multi-angle video feeds of a target object with portable electronic devices and generates a user-controllable three-dimensional model by performing various 3D reconstruction calculations and procedures in a scalable cloud computing network. In one example, a HoloCloud system comprises a plurality of common consumer-level video recording devices (e.g. smartphones, camcorders, digital cameras, etc.) positioned in various angles surrounding a target object (e.g. a human, an animal, a moving object, etc.), a scalable number of graphic processing units (GPU's) in a scalable cloud computing platform, a 3D pre-processing module, a 3D reconstruction module, a background 3D graphics content, a 360-degree virtual reality or video content, and a dynamic 3D model created by the 3D reconstruction module. In one embodiment, the 3D pre-processing module and the 3D reconstruction modules are graphics processing software executed in the scalable number of graphic processing units (GPU's). In another embodiment, these modules may be hard-coded specialized semiconductor chipsets or another hardware that operate in conjunction with the GPU's to provide 3D processing and reconstruction.

FIG. 1 shows a process diagram (100) for rapid three-dimensional model generation from a dedicated real-time model reconstruction studio with multiple camera angles, in accordance with an embodiment of the invention. In a preferred embodiment of the invention, the dedicated real-time model reconstruction studio with multiple camera angles is called "HoloPortal." HoloPortal is a 3D model creation studio with a real-time or near real-time 3D reconstruction system.

This 3D model creation studio is configured to place a target object (e.g. a human, an animal, or another moving object) in a designated area of the 3D model creation studio that positions a plurality of cameras in various angles around the designated area to capture multi-angle video footages of the target object. Then, the multi-angle video footages are processed, transformed, and reconstructed as dynamic 3D models, which may include 3D mesh models, textures for all related frames, and movement frames associated with the target object. After the dynamic 3D models, also called herein as "3D body doubles" are generated from the HoloPortal, the dynamic 3D models can be stored in a 3D model database, which may be dynamically linked to an electronic social platform for sharing, monetizing, and viewing a variety of dynamic 3D models stored in the 3D model database. These dynamic 3D models may be generated in 3D model formats such as OBJ's or COLLADA's.

In one example, as shown in the process diagram (100) of FIG. 1, HoloPortal first records multi-angle videos from a multiple number of cameras surrounding the designated area. Then, the multi-angle videos undergo silhouette extractions, 3D voxel generation, 3D mesh generation, deformed 3D mesh generation, and texture-on-mesh generation to create a 3D model, or a "3D body double" model through a variety of data transformations and graphics reconstructions executed on graphics processing units incorporated in or associated with the HoloPortal.

Preferably, the HoloPortal can generate 3D models (e.g. "3D body doubles") and 3D contents in real-time or near real-time, without lengthy and laborious conventional methods of 3D content generation processes that can take many hours to many months. Furthermore, the 3D models generated from the HoloPortal can be utilized in as characters of a 3D computerized game, a 3D animation movie, an augmented reality application, or a virtual reality application. For example, a life-sized 3D model (e.g. a "three-dimensional (3D) body double" model created after the multi-angle video capture of a human figure) may be created and displayed in an augmented reality or virtual reality goggle or in an another wearable electronic device. Moreover, a computerized 3D model created from the HoloPortal may be physically manufactured with a 3D printing machine located within or outside the HoloPortal for commercial, promotional, business, or transactional purposes.

Figure 2:
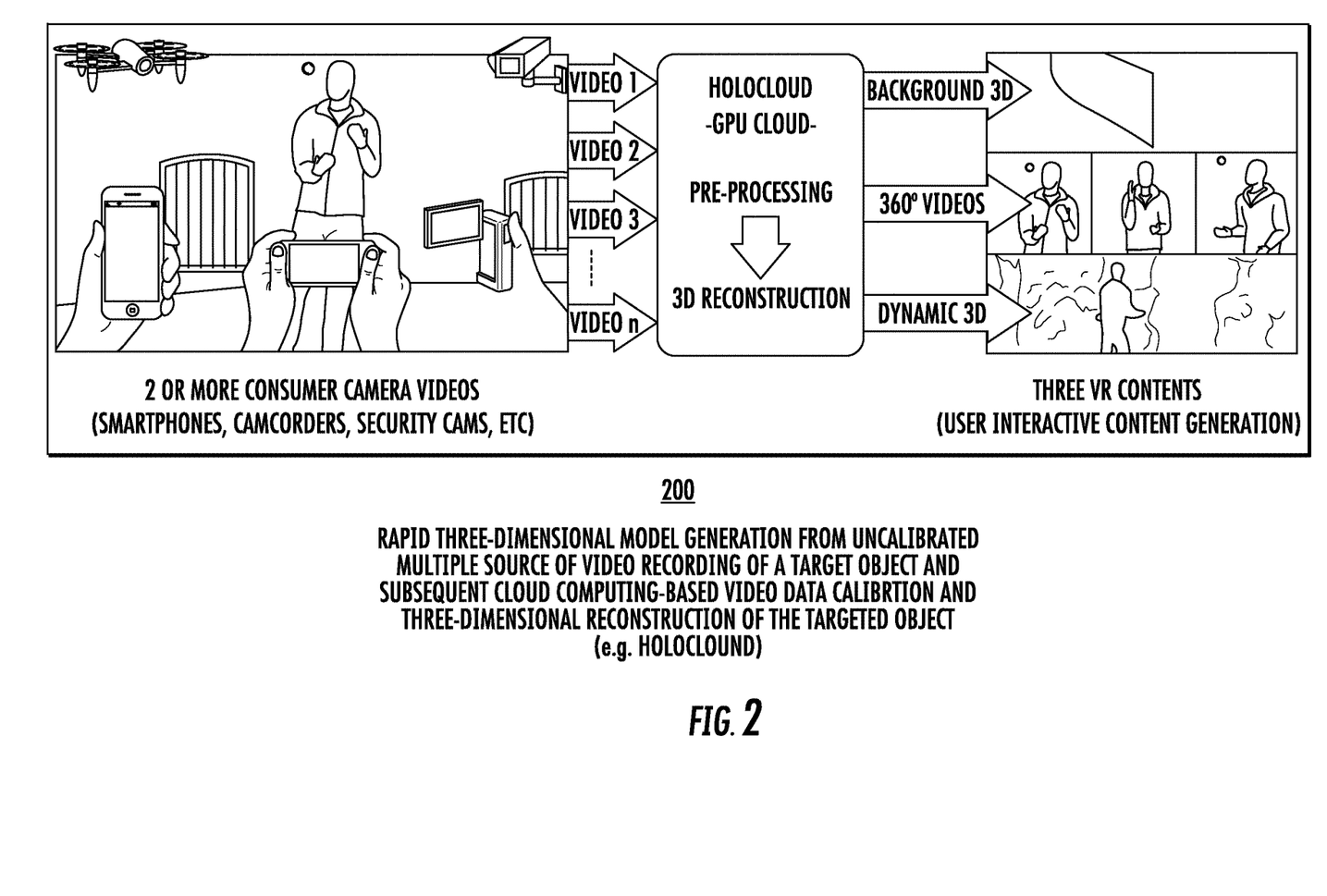
FIG. 2 shows a rapid three-dimensional model generation from uncalibrated multiple sources of video recording of a targeted object and subsequent cloud computing-based video data calibration and three-dimensional reconstruction of the targeted object, in accordance with an embodiment of the invention.

FIG. 2 shows a rapid three-dimensional model generation process (200) from uncalibrated multiple sources of video recording of a targeted object and subsequent cloud computing-based video data calibration and three-dimensional reconstruction of the targeted object, in accordance with an embodiment of the invention. In a preferred embodiment of the invention, a novel electronic system that encompasses this rapid three-dimensional model generation process (200) is called "HoloCloud." Typically, the novel electronic system (i.e. HoloCloud) comprises a plurality of common consumer-level video recording devices (e.g. smartphones, camcorders, digital cameras, etc.) positioned in various angles surrounding a target object (e.g. a human, an animal, a moving object, etc.), a scalable number of graphic processing units (GPU's) in a scalable cloud computing platform, a 3D pre-processing module, a 3D reconstruction module, a background 3D graphics content, a 360-degree virtual reality or video content, and a dynamic 3D model created by the 3D reconstruction module.

As shown in the rapid three-dimensional model generation process (200) of FIG. 2, the plurality of common consumer-level video recording devices generate a plurality of digitized video feeds (e.g. Video 1, Video 2, . . . Video n) in various angles for a target object, and then utilizes an integrated or standalone wireless transceiver (e.g. a cellular transceiver, a WiFi LAN transceiver, etc.) to transmit the plurality of digitized video feeds to a HoloCloud graphics processing unit (GPU) in a cloud computing platform. In a preferred embodiment, the HoloCloud GPU incorporates a pre-processing module and a 3D reconstruction module. The pre-processing module is configured to calibrate temporal, spatial, and photometrical variables of the multi-angle digitized video feeds, and is also able to generate background 3D geometry and 360-degree virtual reality video. The 3D reconstruction module is configured to provide depth map computations, voxel grid reconstructions, and deformed mesh generations for eventual generation of dynamic 3D models.

After numerous internal stages of video extractions, transformations, and reconstruction through the HoloCloud GPU, the background 3D graphics content, the 360-degree virtual reality or video content, and the dynamic 3D model are electronically generated and subsequently utilized as 3D figures or graphics in a virtual reality application, in an augmented reality application, or in a 3D printing of a physical 3D model made of plastic, rubber, or metallic composite materials.

FIG. 3 shows pre-processing and reconstruction procedures (300) in cloud computing-based video data calibration and three-dimensional reconstruction of the targeted object, in accordance with an embodiment of the invention. In this embodiment of the invention, a multiple number of common consumer-level video recording devices generate a plurality of digitized video feeds (e.g. Video 1, Video 2, . . . Video n)

in various angles for a target object, and then transmit the plurality of digitized video feeds to a HoloCloud graphics processing unit (GPU) in a cloud computing platform. Typically, the cloud computing platform is a collective number of graphics computing machines that are dynamically scalable to deploy and assign a flexible number of GPU's for parallel processing, depending on the intensity of graphics computation, transformation, and reconstruction requirements for the plurality of digitized video feeds. For example, a larger number of GPU's may be assigned to perform 3D graphics processing if the plurality of digitized video feeds has a high video feed count, long durations, and/or higher resolutions. In contrast, a smaller number of GPU's may be assigned to perform 3D graphics processing if the plurality of digitized video feeds has a low video feed count, short durations, and/or lower resolutions.

As shown in the pre-processing and reconstruction procedures (300) in cloud computing-based video data calibration and three-dimensional reconstruction of the targeted object, each HoloCloud GPU can incorporate a pre-processing module and a 3D reconstruction module. The pre-processing module executes calibration of temporal, spatial, and photometrical variables of the multi-angle digitized video feeds, and is also able to generate background 3D geometry and 360-degree virtual reality video. The 3D reconstruction module, on the other hand, performs depth map computations, voxel grid reconstructions, and deformed mesh generations for eventual generation of dynamic 3D models or characters.

After numerous internal stages of video extractions, transformations, and reconstruction through one or more HoloCloud GPU's that are typically configured to scale and parallel-process a varying amount of workload for 3D content generation, the background 3D geometry graphics content, the 360-degree virtual reality video content, and the dynamic 3D model are electronically generated and subsequently utilized as 3D figures or graphics in a virtual reality application, in an augmented reality application, or in a 3D printing of a physical 3D model made of plastic, rubber, or metallic composite materials.

The novel electronics system utilizing a plurality of common consumer-level video recording devices for multi-angle video feeds of a target object and a scalable number of HoloCloud GPU's for video extractions, transformations, and reconstruction of dynamic 3D models enables casual consumers to capture and generate 3D graphics contents rapidly and inexpensively, without necessitating specialized 3D content recording equipment and/or high-powered 3D graphics computing equipment on site that are typically required in conventional 3D content generation. Furthermore, by wirelessly transmitting the recorded multi-angle video feeds to a scalable number of HoloCloud GPU's executed in a cloud computing network that processes high-powered graphics computing tasks to generate dynamic 3D models, the casual consumer is not required to have an expert knowledge of 3D graphics pre-processing and reconstruction processes that may be electronically executed by a third-party HoloCloud service operator. Therefore, various embodiments of the present invention enable convenient and pervasive casual user-created dynamic 3D models and 3D contents, which were previously difficult to generate with conventional 3D content generation solutions.

Figure 4:
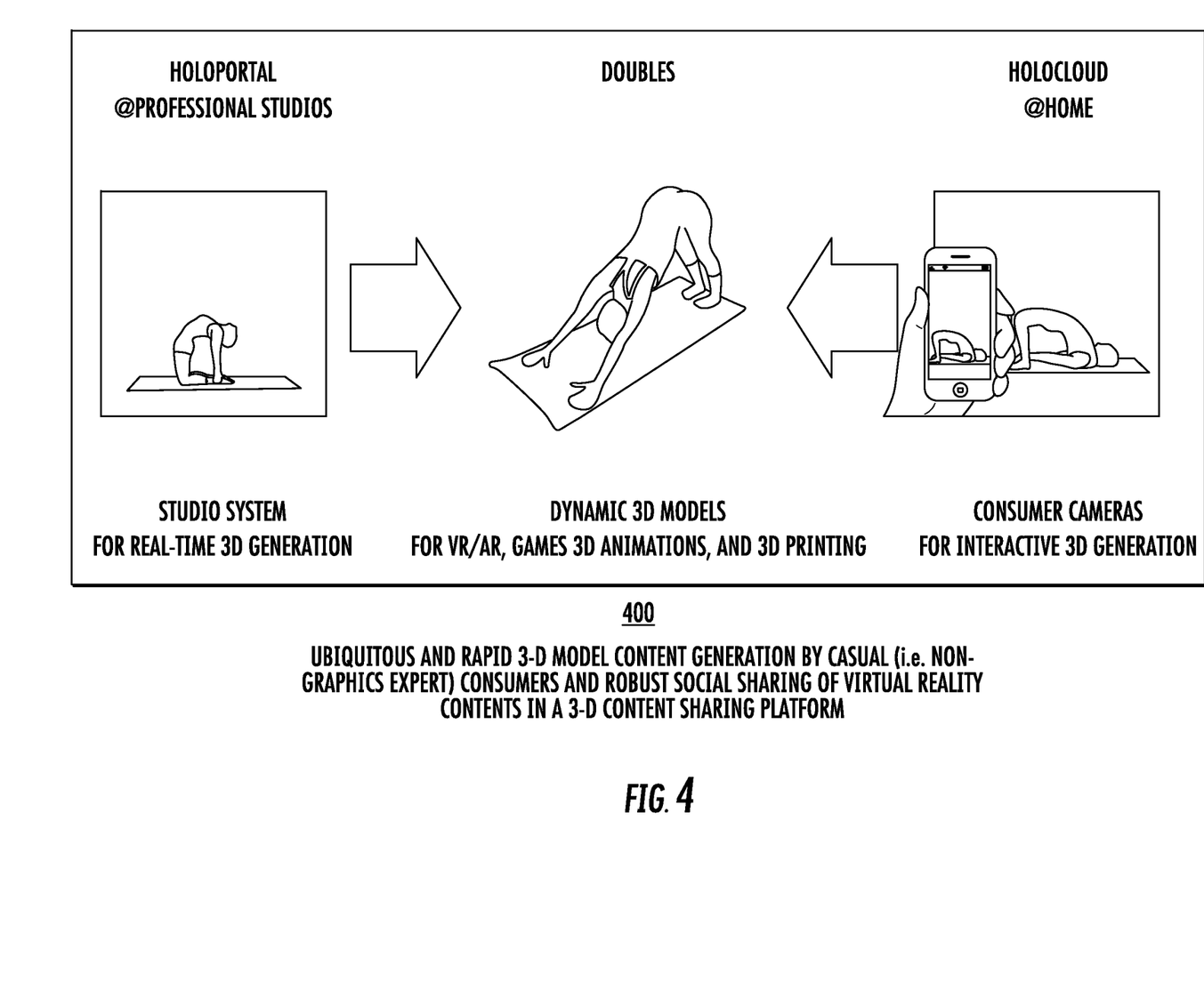
FIG. 4 shows a ubiquitous and rapid three-dimensional model content generation by casual (i.e. non-graphics expert) consumers and robust social sharing of virtual reality contents in a 3D content sharing platform, in accordance with one or more embodiments of the invention.

FIG. 4 shows a novel process (400) embodying two methods of ubiquitous and rapid three-dimensional model content generation by casual (i.e. non-graphics expert) consumers and robust social sharing of virtual reality contents in a 3D content sharing platform, in accordance with one or more embodiments of the invention. A first method of ubiquitous and rapid three-dimensional model content generation involves a dedicated 3D content generation studio (i.e. "HoloPortal") that allows a casual consumer to walk into a HoloPortal facility to capture multi-angle video feeds from professionally installed multiple cameras surrounding a targeted area in the HoloPortal for a dynamic 3D model generation from onsite graphics processing units. Furthermore, a second method of ubiquitous and rapid three-dimensional model content generation involves a plurality of consumer cameras at any location of a casual consumer's choice to capture multi-angle video feeds around a target object, wherein the multi-angle video feeds are subsequently transmitted to a cloud computing resource specializing in 3D graphics processing to generate a dynamic 3D model. The second method of the dynamic 3D model generation is called "HoloCloud," as described previously and as also shown in FIG. 4.

Once dynamic 3D models are generated by a HoloPortal system or a HoloCloud system, they can be incorporated or synthesized into various electronic applications, such as virtual reality applications, augmented reality applications, 3D animation movies, and 3D-printed physical 3D models, as shown in FIG. 4. For example, a dynamic 3D model can be displayed as a life-sized model in a wearable computing device, such as a virtual reality goggle or a hologram display projector. In another example, a physical 3D model made of plastic, metallic, or composite materials may be created by a 3D printer. Furthermore, the dynamic 3D models can be uploaded, listed, and shared on an electronic 3D model and content sharing platform that connects content creators, distributors, service providers, and content viewers. The electronic 3D model and content sharing platform may also provide paid viewing as well as complimentary viewing features based on content access permission parameters configured by the content creators and/or the distributors.

Figure 5:
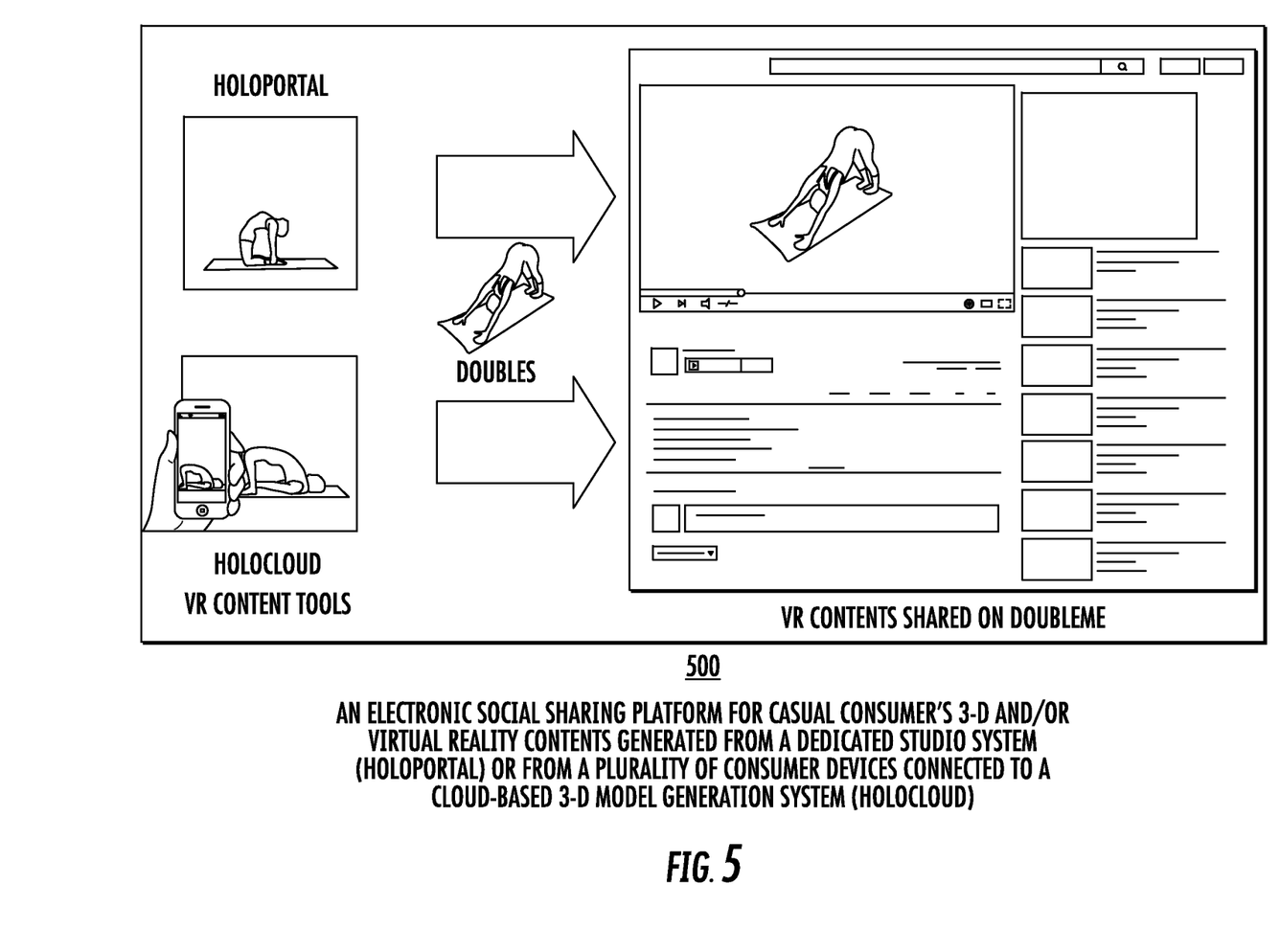
FIG. 5 shows an electronic social sharing platform for casual consumer's 3D and/or virtual reality contents generated from a dedicated studio system (HoloPortal) or from a plurality of consumer devices connected to a cloud-based 3D model generation system (HoloCloud), in accordance with an embodiment of the invention.

FIG. 5 shows an electronic social sharing platform (500) for casual consumer's 3D and/or virtual reality contents generated from a dedicated studio system (HoloPortal) or from a plurality of consumer devices connected to a cloud-based 3D model generation system (HoloCloud), in accordance with an embodiment of the invention. In a preferred embodiment, the electronic social sharing platform (500) is configured to upload, list, and share 3D model animations and 3D contents that are typically created by casual content creators (e.g. consumers with no computer graphics creation expertise or training). The electronic social sharing platform (500) may also accommodate pay-per-view or timed rental transactions that are required by the casual content creators and purchased by content viewers who are also accessing the electronic social sharing platform (500).

In a preferred embodiment, the electronic social sharing platform (500) is connected to a 3D model and content database, and is configured to display dynamic 3D models and 3D contents through a display user interface, as shown in FIG. 5. Preferably, the dynamic 3D models and the 3D contents are initially created from a HoloPortal system or a HoloCloud system by a casual (i.e. non computer graphics expert) content creator, who then uploads the dynamic 3D models and the 3D contents (e.g. "3D body doubles") to the electronic social sharing platform (500) for listing and managed distribution of contents to content viewers. In some embodiments of the invention, the electronic social sharing platform (500) may be operated and managed by a content distributor or a content service provider. In other embodiments of the invention, the electronic social sharing platform (500) may be operated and managed by a group of content creators and/or content viewers.

Moreover, the electronic social sharing platform (500) may authorize a convent viewer to download a desired dynamic 3D model or 3D content as a 3D file that can be played on a standalone 3D content player unit, or instead authorize the content viewer to play the desired dynamic 3D model or 3D content on an online web viewer unit linked to the electronic social sharing platform (500). The online web viewer unit or the standalone 3D content player unit may be executable and displayable from a desktop computer, a notebook computer, a tablet computer, a smart phone, a specialized 3D display device, or another electronic device. If dynamic 3D model and/or 3D content files are downloaded directly to a consumer's electronic device, the dynamic 3D model and/or 3D content files may be repurposed as objects synthesized in 3D games, 3D animations, 3D games, virtual reality contents, or augmented reality contents. Furthermore, the dynamic 3D model and/or 3D content files may also be utilized in a 3D printing machine to manufacture a physical 3D model.

Figure 6:
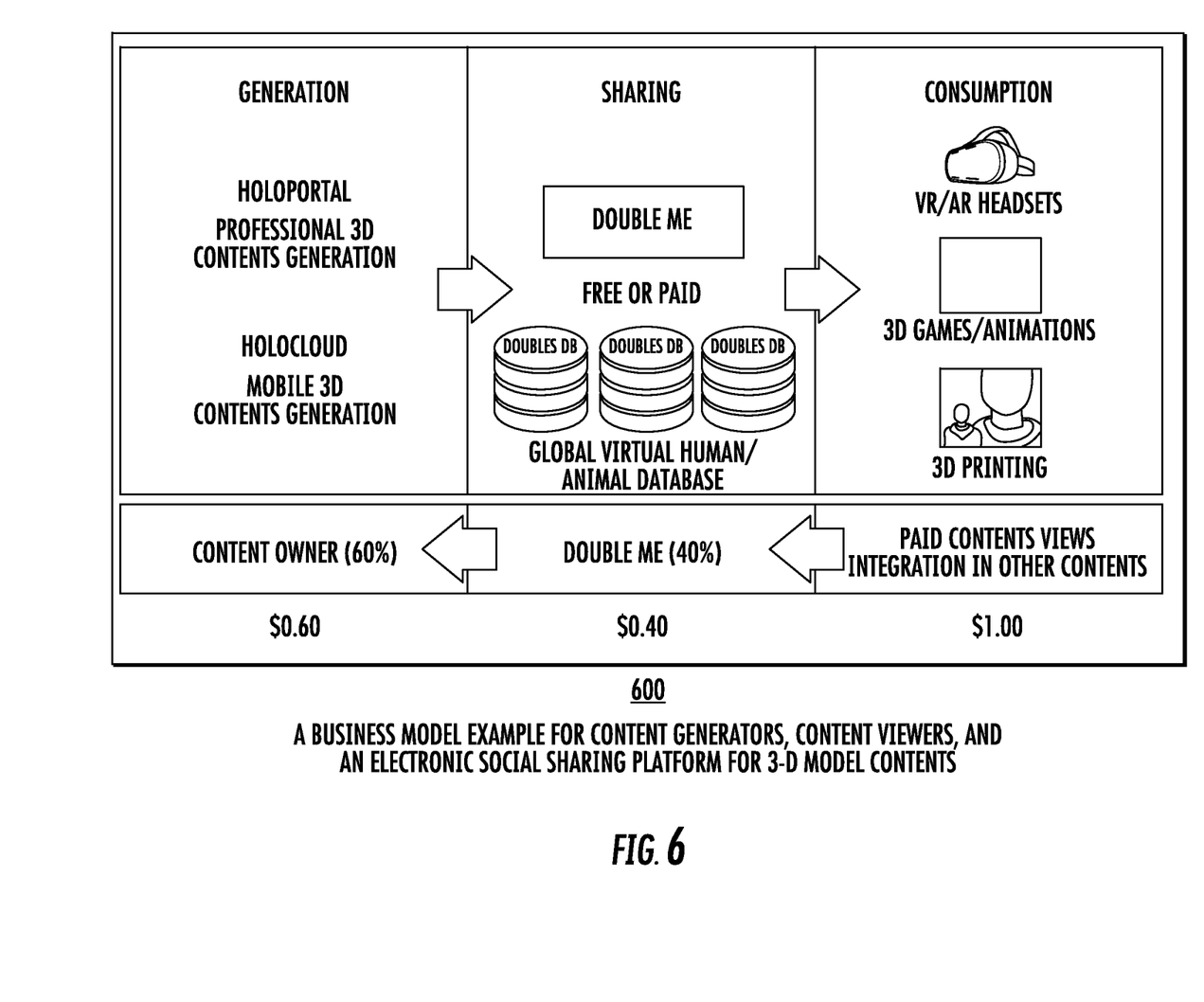
FIG. 6 shows a business model example for content generators, content viewers, and an electronic social sharing platform for 3D model contents, in accordance with an embodiment of the invention.

FIG. 6 shows a business model example (600) for content generators, content viewers, and an electronic social sharing platform for 3D model contents, in accordance with an embodiment of the invention. In this business model example (600), a content viewer who purchases a virtual reality or augmented reality 3D content, a 3D animation, a 3D game, or a 3D printer-produced object pays a specified fee (e.g. $1.00) through the electronic social sharing platform for 3D model contents. Then, the specified fee (e.g. $1.00) is divided between a service operator (e.g. a company called "DoubleMe") and a content creator/owner who utilized a HoloPortal system or a HoloCloud system to generate dynamic 3D models and 3D contents, as shown in FIG. 6.

In a preferred embodiment of the invention, the service operator may provide and manage a 3D content database and the electronic social sharing platform for 3D model contents that incorporate an online 3D content player and/or a 3D file download feature to the content viewer. Furthermore, in some cases, the service operator may also provide and manage the HoloPortal system and the HoloCloud system to enable the content creator/owner to generate the dynamic 3D models and 3D contents. As an example of compensation, the service operator may take 40 percent (e.g. $0.40) of the specified fee (e.g. $1.00) paid by the content viewer, while the content creator/owner may take 60 percent (e.g. $0.60) of the specified fee (e.g. $1.00). As the business model example (600) is merely an example of such financial compensation arrangements, specific compensation structures for various embodiments of the present invention may vary, with various proportions of the specified fee assigned to the service operator and the content creator/owner. Furthermore, in some embodiments of the invention, the service operator may simply be a non-profit group of content viewers and content creators/owners.

In the preferred embodiment of the invention, the specified fee (e.g. $1.00) required for downloading or watching a particular 3D model or 3D content may be set by the content creator/owner and/or the service operator. Furthermore, the specified fee may vary, depending on the content viewer's request to download or simply replay the particular 3D model or 3D content on an online 3D content player. For example, the specified fee may be higher for a locally-downloaded importable file of the particular 3D model or 3D content, while the specified fee may be lower for a mere online replay of the particular 3D model or 3D content.

Figure 7:
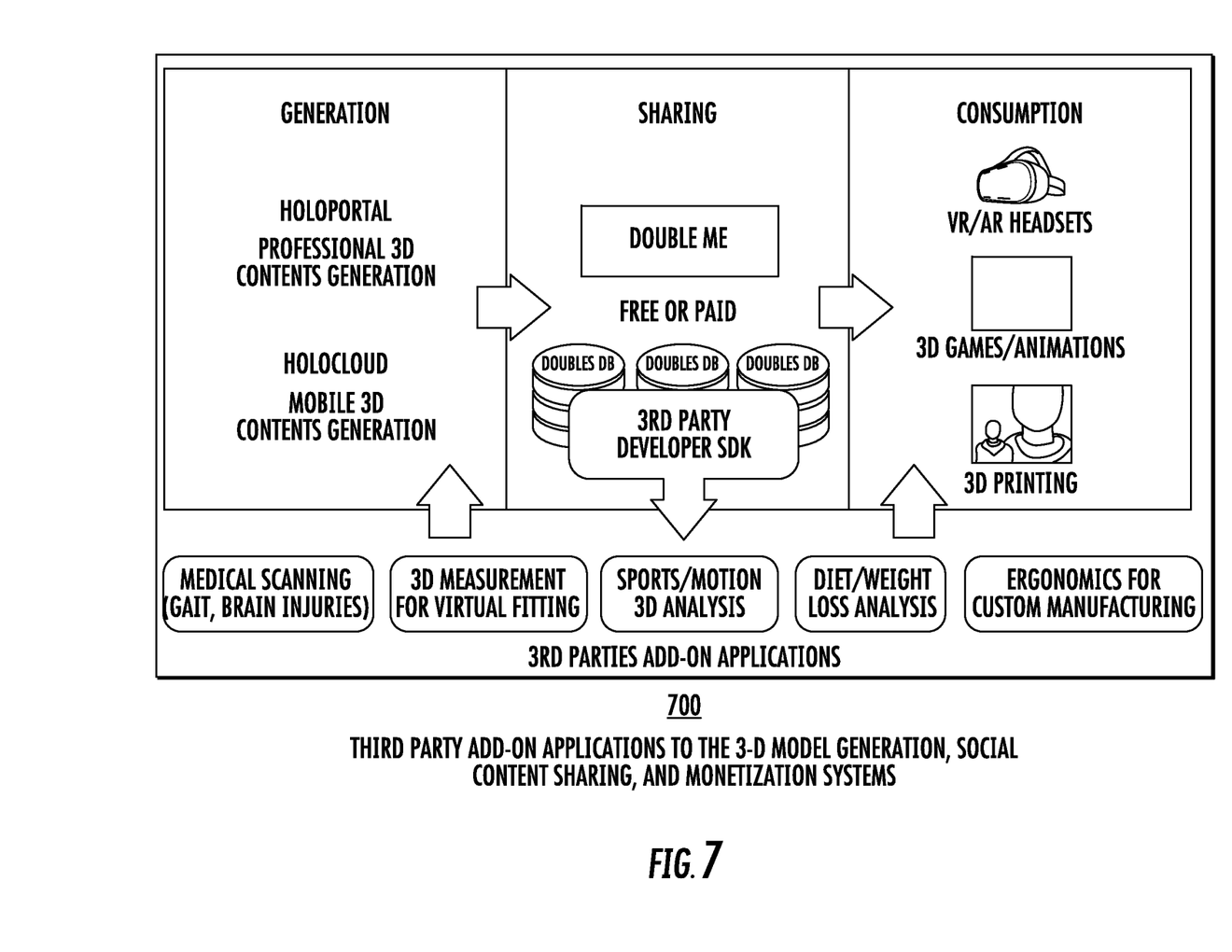
FIG. 7 shows third party add-on applications to the 3D model generation, social content sharing, and monetization systems, in accordance with an embodiment of the invention.

FIG. 7 shows third party add-on applications (700) to the 3D model generation, social content sharing, and monetization systems, in accordance with an embodiment of the invention. Examples of third party add-on applications (700) include, but are not limited to, 3D medical scanning applications (e.g. for gait and brain injuries), 3D virtual-fitting applications, sports or motion 3D analysis applications, diet/weight loss analysis applications with 3D modeling, and 3D ergonomics analysis applications for custom manufacturing applications.

The third party add-on applications may utilize dynamic 3D models created from a HoloPortal system or a HoloCloud system by content creators or owners. Furthermore, the third party add-on applications may be configured to transmit 3D modeling data to or receive 3D modeling data from 3D social content sharing and 3D content monetization systems. Moreover, a service operator for an electronic social sharing platform for 3D model contents may provide a third party developer software development kit (SDK) to third-party application developers to create a diverse set of third party add-on applications for the 3D model generation, social content sharing, and monetization systems, as disclosed in various embodiments of the present invention.

One or more rapid three-dimensional model generation systems, such as HoloPortal and HoloCloud systems, and their methods of operations have been disclosed in the descriptions above and also in the corresponding drawings. Various embodiments of the present invention exhibit several advantages over conventional electronic methods and systems for 3D content generation. For example, an embodiment of the present invention provides a novel cloud-based electronic system that can inexpensively capture live target objects as multiple-angle videos and rapidly generate 3D models with common consumer video recording equipment and cloud computing resources, at a fraction of a cost for producing 3D models using conventional 3D model generation equipment.

Furthermore, embodiments of the present invention provide convenient and flexible methods and systems for rapidly capturing target objects as video data and reconstructing 3D computerized models by utilizing either a dedicated professional-level 3D model portal studio or consumer video recording devices communicating with scalable cloud computing resources. These convenient and flexible methods and systems for 3D model generation lower the barrier of entry for an everyday consumer to create, share, and monetize 3D models, thus encouraging a widespread consumer utilization of casual user-created 3D models over the Internet.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the claims, which will be formally recited in a corresponding non-provisional application.

What is claimed is:

1. A three-dimensional (3D) body double-generating electronic system that provides two separate 3D model generation pathways as a combined turnkey solution to a casual consumer who is not a graphics expert, the system comprising:

a three-dimensional (3D) model creation studio that incorporates cameras positioned on a multiple number of angles around a stage, where a first target object brought into the 3D model creation studio by the casual consumer is placed for video footage recording at the multiple number of angles around the stage, and wherein the 3D model creation studio further includes a near real-time 3D reconstruction electronic system to create a first 3D body double model that resembles the first target object brought in by the casual consumer;

a cloud-based 3D model creation platform that utilizes portable video recording devices positioned at multiple-angle views around a second target object and a scalable number of graphics processing units (GPU's) in a cloud computing resource for creation of a second 3D body double model that resembles the second target object;

a 3D model and content database that stores the first 3D body double model from the 3D model creation studio and the second 3D body double model from the cloud-based 3D model creation platform, wherein the two separate 3D model generation pathways provided by the 3D model creation studio and the cloud-based 3D model creation platform are the combined turnkey solution to the casual consumer who does not have operational knowledge or ownership of specialized 3D equipment for creating 3D body double models;

an electronic 3D content sharing software executed on a computer server connected to the 3D model and content database, wherein the electronic 3D content sharing software controls the computer server to upload, list, transmit, and share 3D model animations and 3D contents that are created from the 3D model creation studio or the cloud-based 3D model creation platform;

a client-side 3D content viewer and management user interface executed on a notebook computer, a desktop computer, a mobile communication device, or a web server, wherein the client-side 3D content viewer and management user interface enables a user to purchase, sell, transmit, receive, or playback a 3D content incorporating the first 3D body double model or the second 3D body double model via the electronic 3D content sharing software and the 3D model and content database;

a plurality of wireless transceivers integrated into the portable video recording devices, wherein the wireless transceivers transmit multiple-angle video data streams from the portable video recording devices to the scalable number of GPU's in the cloud computing resource; and the cloud computing resource comprising one or more cloud computing servers that include one or more GPU's, wherein the one or more cloud computing servers are connected to each other to formulate a scalable cloud computing network, and wherein the scalable cloud computing network allocates and manages the scalable number of GPU's to achieve a creation of the second 3D body double model based on a particular calculation load requirement for the graphical transformations associated with the second target object.

2. The three-dimensional body double-generating electronic system of claim 1, wherein the scalable cloud computing network allocates a larger number of GPU's to process the graphical transformations associated with the second target object when the multiple-angle video data streams have a higher calculation load requirement due to at least one of a higher video feed count, a longer duration, or a higher resolution for the multiple-angle video data streams.

3. The three-dimensional body double-generating electronic system of claim 1, wherein the scalable cloud computing network allocates a smaller number of GPU's to process the graphical transformations associated with the second target object when the multiple-angle video data streams has a lower calculation load requirement due to at least one of a lower video feed count, a shorter duration, or a lower resolution for the multiple-angle video data streams.

\* \* \* \* \*